United States Patent
Fulde (10) Patent No.: US 11,247,172 B2
(45) Date of Patent: Feb. 15, 2022

(54) METHOD FOR SEPARATING OFF AND IMMOBILIZING CARBON DIOXIDE AND/OR CARBON MONOXIDE FROM AN EXHAUST GAS

(71) Applicant: Marek Fulde, Offenbach (DE)

(72) Inventor: Marek Fulde, Offenbach (DE)

(73) Assignee: FLD TECHNOLOGIES GMBH, Offenbach am Main (DE)

( * ) Notice: Subject to any disclaimer, the term of this patent is extended or adjusted under 35 U.S.C. 154(b) by 70 days.

(21) Appl. No.: 16/340,776

(22) PCT Filed: Oct. 13, 2017

(86) PCT No.: PCT/EP2017/076201
§ 371 (c)(1),
(2) Date: Apr. 10, 2019

(87) PCT Pub. No.: WO2018/069504
PCT Pub. Date: Apr. 19, 2018

(65) Prior Publication Data
US 2020/0047120 A1    Feb. 13, 2020

(30) Foreign Application Priority Data
Oct. 13, 2016   (DE) .......................... 102016219990.0

(51) Int. Cl.
*B01D 53/86* (2006.01)
*B01D 53/62* (2006.01)
(Continued)

(52) U.S. Cl.
CPC ............. *B01D 53/90* (2013.01); *B01D 53/62* (2013.01); *B01D 53/86* (2013.01); *B01D 53/864* (2013.01);
(Continued)

(58) Field of Classification Search
None
See application file for complete search history.

(56) References Cited

U.S. PATENT DOCUMENTS

| 2,716,053 A | 7/1950 | Mayland |
| 2,992,075 A | 7/1961 | De Galocsy |
| 2016/0226088 A1 | 8/2016 | Fulde |

FOREIGN PATENT DOCUMENTS

| CN | 1346786 A1 | 5/2002 |
| DE | 102007037672 A1 | 2/2009 |

(Continued)

OTHER PUBLICATIONS

Helmeth Project, "Methanation Process." Published online on Dec. 13, 2014 at http://www.helmeth.eu/index.php/technologies/methanation-process (viewed on Apr. 27, 2021 at https://web.archive.org/web/20141213110126/http://www.helmeth.eu/index.php/technologies/methanation-process ).*

(Continued)

*Primary Examiner* — Daniel Berns
(74) *Attorney, Agent, or Firm* — J.A. Lindeman & Co. PLLC (57) ABSTRACT

The invention relates to a method for separating off and immobilizing carbon dioxide and/or carbon monoxide from an exhaust gas (18). In the method, a stoichiometric ratio of carbon dioxide to hydrogen, and/or of carbon monoxide to hydrogen, which is suitable for a methanation reaction is set by virtue of a corresponding quantity of hydrogen or alternatively carbon dioxide and/or possibly carbon monoxide being supplied, with an auxiliary gas (24), to the exhaust gas (18). Subsequently, a catalytic reaction is performed in which, as starting products, carbon dioxide and/or carbon monoxide and hydrogen are converted into methane and water. The methane is separated off from the product of the catalytic reaction and is subsequently split into carbon and (Continued)

hydrogen, wherein the carbon takes solid form. The split-off carbon is collected and disposed of.

10 Claims, 2 Drawing Sheets (51) Int. Cl.
    *B01D 53/90*     (2006.01)
    *C01B 3/16*     (2006.01)
    *C01B 3/24*     (2006.01)
    *C01B 3/58*     (2006.01)
    *C25B 1/04*     (2021.01)
    *C07C 1/04*     (2006.01)
    *C07C 1/12*     (2006.01)

(52) U.S. Cl.
    CPC .......... *B01D 53/8671* (2013.01); *C01B 3/586* (2013.01); *C07C 1/046* (2013.01); *C07C 1/12* (2013.01); *B01D 2251/202* (2013.01); *B01D 2256/245* (2013.01); *B01D 2257/108* (2013.01); *B01D 2257/502* (2013.01); *B01D 2257/504* (2013.01)

(56) References Cited

FOREIGN PATENT DOCUMENTS

| | | |
|---|---|---|
| DE | 102012007136 A1 | 10/2013 |
| DE | 102012214907 A1 | 10/2013 |
| DE | 102012105736 A1 | 1/2014 |
| DE | 102013112205 A1 | 5/2014 |
| DE | 102013020511 A1 | 6/2015 |
| WO | 2015/044407 A1 | 4/2015 |

OTHER PUBLICATIONS

"ECRA CCS Project—Report on Phase III"; European Cement Research Academy; Duesseldorf; Mar. 2012.
C. Kammann et al., "Biochar: A way to permanent I carbon sequestration?" Environmental Observation and Climate Impact Research Station Linden, Hessian State Office for Environment and Geology, URL: http://www.uni-giessen.de/cms/ulk), Apr. 2010.
International Preliminary Report on Patentability and Written Opinion for PCT International Application No. PCT/EP2017/076201, dated Apr. 16, 2019.

* cited by examiner

Fig. 1

METHOD FOR SEPARATING OFF AND IMMOBILIZING CARBON DIOXIDE AND/OR CARBON MONOXIDE FROM AN EXHAUST GAS

The invention relates to a process for separation and immobilization/sequestration of greenhouse-effective substances, such as carbon dioxide and/or carbon monoxide from offgases.

Such processes are known to those skilled in the art as "carbon dioxide capture and storage" (CCS). The sequestration of greenhouse gases comprises a separation of carbon dioxide from industrial sources and power plants, transport to the storage site and finally permanent storage of $CO_2$ insulated from the atmosphere.

The offgases formed during power generation or in industrial processes are typically rich in the greenhouse gas (GHG) carbon dioxide. Carbon monoxide whose climate-damaging effect has not yet been confirmed is likewise a potential environmental risk. In addition to greenhouse gases the offgases consist predominantly of nitrogen and of other air constituents such as argon or oxygen. The concentration of oxygen is relatively low (2 to 6 vol %) since it is almost completely consumed in the combustion. As a consequence of the processes employed industrial offgases may comprise further gas components such as for example hydrogen or carbon monoxide.

To avoid GHG emissions, the known CCS process comprises separation and a subsequent storage of $CO_2$. When using this process, the offgas to be treated is initially freed from particles and sulfur compounds. In the subsequent step, $CO_2$ is separated from the offgas, compressed, optionally transported away and stored underground.

It is a point of contention in science whether permanent binding of $CO_2$ to minerals takes place under these conditions or whether renewed releases into the atmosphere are to be expected. Furthermore, compression of $CO_2$ under high pressure could result in earthquakes. The mixing and dissolution of carbon dioxide with groundwater could also bring about so-called "cold geysers" which would likewise cause renewed emissions.

Another aspect hindering the utilization of CCS technology is the lack of infrastructure that would be required for the transport of $CO_2$. The reason for this is that emissions sources such as power plants or cement works are far away from suitable $CO_2$ storage sites which would necessitate the construction of suitable pipelines.

Document DE 10 2013 112 205 A1 indicates that the carbon produced by thermal decomposition of methane may be readily stored on a long-term basis in old coal seams or elsewhere.

Document DE 10 2007 037 672 A1 describes a process for harmonizing electricity supply/demand profiles via intermediate storage means and incorporation of $CO_2$ utilization. According to this process pure $CO_2$ is obtained from the $CO_2$-containing offgas and intermediately stored. A portion of the stored $CO_2$ is used for hydrogenation to afford hydrocarbons which may in turn be combusted in power plants for power generation. The remaining carbon dioxide is sent for end storage according to a known CCS process. This process does not provide for cracking of hydrocarbons. Storage of carbon in solid form is not carried out.

WO 2015/044407 describes a process for storage of electricity from renewable sources. Pure hydrogen obtained by electrolysis of water is reacted with pure $CO_2$ or a $CO_2/CO/H_2$ mixture to afford methane. Methane is intermediately stored and subsequently cracked into carbon and hydrogen. Carbon is reused for producing $CO_2$ or a $CO_2/CO/H_2$ mixture. Hydrogen is sent for energetic recovery, for example for power generation. Carbon dioxide is not stored; the carbon is completely recirculated in the process.

The present invention may be regarded as having for its object to immobilize climate-active offgases, thus permanently and safely removing from the atmosphere and permanently storing carbon.

DISCLOSURE OF THE INVENTION

A process for separation and immobilization of carbon dioxide and/or carbon monoxide from an offgas is proposed. The offgas is in particular obtained by combustion of fossil fuels in a power plant, as a byproduct in an industrial process or as an extraction gas in the extraction of fossil fuels. The process comprises the steps of:

a) establishing a stoichiometric ratio of carbon dioxide to hydrogen and/or of carbon monoxide and hydrogen which is suitable for a methanization reaction by supplying the offgas with a corresponding amount of hydrogen or alternatively carbon dioxide and/or carbon monoxide by means of an additive gas, b) performing a catalytic reaction in which the reactants carbon dioxide and/or carbon monoxide and also hydrogen are converted into methane and water, c) separating the methane from the product of the catalytic reaction, d) cracking the methane into carbon and hydrogen, wherein the carbon is generated as a solid, e) collecting the cracked carbon and f) landfilling or end-storing the collected carbon.

The offgas may be an offgas formed upon combustion of fossil fuels in a power plant for example. The offgas may for example also be a byproduct formed in an industrial process or the offgas may be an extraction gas generated in the extraction of fossil fuels. These offgases which are normally released into the atmosphere are collected after their formation and treated with the proposed process.

The offgas is preferably a mixture of at least two components and the offgas preferably comprises at least carbon dioxide or carbon monoxide as one component. The offgas may moreover comprise as further components at least one inert gas such as nitrogen or argon, wherein the at least one inert gas remains in the offgas after the separation according to step c). In addition to inert gases the offgas may contain yet further components which exhibit neutral behavior in a catalytic reaction performed in step b). One example of such a neutral component is water vapor. The neutral components may remain in the offgas after separation of the methane. In a preferred embodiment the components of the offgas are selected from carbon dioxide, carbon monoxide, hydrogen and methane, wherein in this case the proposed process completely immobilizes all of these components of the offgas.

The offgases which contain in particular carbon dioxide and/or carbon monoxide as greenhouse-effective substances may in particular be offgases from industrial production processes or from combustion operations and also extraction gases. Extraction gases are generated for example during extraction of fossil fuels such as coal, crude oil or natural gas. One example of an extraction gas is pit gas.

Production of electricity from fossil fuels is the greatest contributor to the generation of offgases.

Equally important as a source of climate-active offgases are industrial processes. One example of an industrial production process is cement production where the emissions of $CO_2$ are very largely attributable to the calcination process. In the production of iron and steel and auxiliary materials required therefor the production offgases contain not only $CO_2$ but also carbon monoxide and methane. Some offgases such as for example blast furnace gas from steel production or coke oven gas contain not only $CO_2$ and $CH_4$ but also the carbon monoxide. The question of whether CO also has a climate-damaging effect has not yet been definitively resolved. The global warming potential factor (GWP factor) of CO is imputed to be 3 kg $CO_2$ equivalent/kg emission. Climate-active offgases may also occur in refineries for example.

Industrial offgases typically contain not only the above-mentioned carbon oxides but also other substances which must be considered during treatment of the offgas. These include inter alia methane, hydrogen, water vapor and the inert gas nitrogen, wherein the proportion of nitrogen may be up to 97 vol %. Further offgas constituents that may be present include impurities such as hydrogen sulfide, mercury and/or heavy metals. These impurities require a pretreatment to achieve prescribed threshold values. Oxygen may also be present in the offgas of power plants in concentrations of up to 6 vol %. Offgases formed during extraction of, for example, natural gas contain not only methane but also $CO_2$ and nitrogen in relevant proportions.

The first step a) of the process comprises supplying the offgas with hydrogen or alternatively carbon dioxide and/or carbon monoxide so that the molar ratio between hydrogen and carbon dioxide and/or between carbon monoxide and hydrogen preferably conforms to the stoichiometric coefficient of the Sabatier reaction $$CO_2 + 4H_2 \rightarrow CH_4 + 2H_2O \quad (1)$$

or of CO methanization $$CO + 3H_2 \rightarrow CH_4 + H_2O \quad (2)$$

In the case of an excess of hydrogen carbon dioxide and/or carbon monoxide are supplied and in the case of a deficit of hydrogen/an excess of carbon oxides hydrogen is supplied.

To establish the stoichiometric ratio it is preferable when the proportions of carbon dioxide and/or of carbon monoxide present in the offgas are measured. Provided that the offgas contains hydrogen as one component it is also preferable when the proportion of hydrogen in the offgas is measured. It is moreover additionally possible to measure the proportion of oxygen present in the offgas. In order to allow a loss of hydrogen resulting from the reaction of hydrogen with oxygen present in the offgas to be compensated, there may additionally be provision for determining the amount of hydrogen in the mixture produced and/or the proportion of oxygen in the offgas. The amount of gas to be supplied is then determined with reference to the offgas volume to be treated and the determined proportions of the individual components in the offgas.

If the offgas is rich in carbon dioxide and/or carbon monoxide, hydrogen is supplied by means of the additive gas. If the offgas is rich in hydrogen, carbon dioxide and/or carbon monoxide are supplied by means of the additive gas.

The hydrogen for the additive gas is preferably produced by means of an electrolysis operation, for example by high temperature steam electrolysis. It is preferable when the waste heat from the offgases is used for producing steam and/or for generating electricity. The electrolysis for producing hydrogen preferably employs, at least partially, electricity from renewable sources. The electrolysis may in particular also employ electricity from renewable sources for which there is presently no demand in the power grid. Further preferred sources of the hydrogen include industrial processes such as NaCl electrolysis for obtaining chlorine where hydrogen is generated as a byproduct.

The oxygen likewise generated in the electrolysis of water may be released into the atmosphere. In a preferred embodiment of the process, the oxygen produced is supplied to a combustion operation in which the offgas to be treated with the described process is formed. This allows the combustion to be performed with pure oxygen or at least with a gas mixture having an oxygen content that is elevated compared to the normal oxygen proportion in the atmosphere. This increases the efficiency of the combustion operation and reduces the proportion of inert gases present in the offgas. This reduces the volume of offgas to be treated. Combustion operations performed with addition of pure oxygen are referred to in the prior art as "oxyfuel" processes.

Carbon dioxide for the additive gas is preferably produced by combustion of carbon-containing fuels such as for example biomass or wastes. The heat thus produced is used in the production process and/or for power generation. It is preferable when the additive gas is a corresponding further offgas which is accordingly likewise treated in the context of this process. The ratio of matter required for CO methanization may likewise be established using carbon monoxide.

The offgas is preferably purified of dust, sulfur-containing compounds and other impurities such as nitrogen oxides, hydrogen chloride, hydrogen fluoride, mercury, other metals and other organic or inorganic substances using customary, known processes before supply of the additive gas.

The second step b) of the process comprises supplying the mixture of the offgas and the added additive gas to a catalytic methanization reaction, wherein carbon dioxide and hydrogen and/or carbon monoxide and hydrogen are converted into methane and water. It is preferable when the catalytic methanization reaction is a Sabatier reaction and/or a CO methanization reaction. With the exception of any hydrogen already present in the offgas the further components present in the offgas are not involved in the methanization reactions. The reactions are preferably carried out at temperatures of 250° C. to 350° C.

Both reactions (1) and (2) are exothermic. The excess heat produced may be utilized in the context of the process, for example for providing steam for a steam electrolysis.

The methane formed in the reactions (1) and (2) is freed from hydrogen and any further components present in the offgas in step c) of the process. The separation of the methane is preferably effected by physical means, in particular by condensation, adsorption or separation with membranes. It is also preferable to separate steam by means of a condensation process.

The separated methane is preferably brought to quality specifications as natural gas and fed into the municipal natural gas network. The methane may alternatively be intermediately stored in a tank. The further components present in the offgas are substantially inert gases such as nitrogen and steam and may be discharged into the environment without issue. The separated methane may be stored in the natural gas network and/or transported to a location where hydrogen is required or to a carbon landfill site.

Offgas formation and carbon landfilling may be realized in one or more spatially separate locations. This is made possible due to the transportability via the municipal natural gas network of the methane into which the offgas has been converted.

The subsequent step d) of the process comprises carrying out cracking of the methane into carbon and hydrogen. If the methane was previously fed into the natural gas network methane is now withdrawn from the natural gas network and cracked into its elements in a cracking process. The cracking is an endothermic and thus requires an external energy source. The cracking conforms to the reaction:

$$CH_4 \rightarrow C + 2H_2 \tag{3}$$

It is preferable when a pyrolysis process is used for the cracking of the methane.

The energy required to perform the reaction (3) is preferably provided in the form of electricity from renewable sources for which there is presently no demand in the power grid, so that no fossil fuels are used. Alternatively a portion of the hydrogen obtained may be used to provide the energy required for the cracking. It is preferable to undertake the cracking at the location where hydrogen is used as fuel, including fuel for fuel cell vehicles, or as a raw material for applications in the chemical industry for example. The carbon is collected and transported to a landfill site.

It is preferable when at least a portion of the hydrogen produced in the cracking is used as a starting material in the chemical industry, as an energy carrier for the generation of electricity and/or heat or as a fuel for vehicles.

The carbon formed as a solid is collected and permanently stored/end-stored. In this way the greenhouse gases "extracted" from the offgases are removed from the atmosphere.

The carbon obtained as a solid is preferably mixed with a carrier before permanent storage/landfilling in order to ensure permanent immobilization of the carbon and particularly safe storage. Carriers that may be employed include for example sand, loam, gravel, building rubble, slags, rocks, wastes, in particular from industrial installations, or a combination of two or more of these materials.

Storage of the immobilized carbon is preferably underground, for example in old mines, in particular potash mines or salt mines. However, the immobilized carbon is also suitable for use as a filler for filling strip mines, excavations, gravel, gypsum or clay pits.

In order to avoid geological damage and to follow environmental protection obligations, disused extraction sites are subjected to extensive cleanup and re-cultivation measures. Both the cavities of underground mines and the pits themselves are filled with mineral material. Suitable materials that may be employed include building rubble, slags, rocks, waste from industrial installations and other industrial wastes having sufficient strength. If carbon alone were used this would first need to be compressed. Mixing of the pulverulent carbon with minerals or wastes has proven advantageous since carbon can penetrate into the porous structure of the minerals and be permanently fixed therein. This makes it possible to achieve a permanent immobilization of the carbon and thus a purifying effect for the atmosphere.

ADVANTAGES OF THE INVENTION

The process proposed according to the invention makes it possible to free gases such as for example industrial offgases or extraction gases from climate-damaging substances such as $CO_2$ and CO. Any methane present in the offgas is advantageously likewise removed. Any hydrogen present in the offgas which would otherwise escape into the atmosphere unused may likewise be utilized. The methanization reaction employs prepurified offgases as the reactant without an upstream complete oxidation of $CH_4$ or CO to $CO_2$ being required.

The conversion of the climate-damaging substances into carbon in solid form substantially simplifies sequestration since a solid rather than a gas is immobilized. Finding a suitable carbon landfill site is much easier than finding suitable storage capacities for gaseous $CO_2$ such as are required for conventional CCS processes.

Landfilling carbon in solid form eliminates the risks of re-emission. Geological risks associated with compressing the gaseous carbon dioxide under high pressure are avoided.

The process broadens the applicability of sequestration of carbon to other greenhouse gases such as carbon monoxide which are not considered in CCS processes. Any methane and hydrogen present are likewise sequestered and utilized. The known CCS processes relate exclusively to the treatment of carbon dioxide. The known CCS processes do effect treatment of methane despite methane having a climate damaging effect far greater than that of $CO_2$.

The process also allows for storage and transport of the electricity from renewable sources independent of a power grid. To this end, the methane formed as an intermediate of the process is transported via an existing natural gas network. The production of hydrogen, which may be used as fuel, provides broad opportunities for sectoral integration between electricity, heat, mobility or use as a feedstock. The methane produced likewise makes it possible to transport the carbon to a landfill site using the existing gas network.

Industrial offgases are often characterized by a high energetic potential. Utilization of the potential for producing steam and for operating a high temperature steam electrolysis in particular contributes to an increased efficiency of the process according to the invention.

One of the options for increasing the efficiency of CCS is the "oxyfuel" process in which pure oxygen or an oxygen-enriched mixture is used for combustion instead of air. Advantageous here is the absence of atmospheric nitrogen or at least a reduction in the proportion of atmospheric nitrogen, thus increasing the concentration of $CO_2$ in the offgas and facilitating separation of $CO_2$. A disadvantage is the need to provide pure oxygen by air separation.

In the proposed process, water or steam electrolysis is a constituent of the process and oxygen is therefore produced as a byproduct in addition to hydrogen. Said oxygen may be used for nitrogen-free/nitrogen-reduced combustion. Air separation would no longer be required. This contributes substantially to increasing the economy of the method. The invention is elucidated by the examples and claims.

EXAMPLES

Working Example 1: Treatment of Offgas From Cement Production

The production of cement clinker forms GHG-rich offgases. Carbon dioxide forms as a result of the dehydration reaction of calcium compounds. Since this reaction is strongly endothermic, it requires a large amount of energy generated by combustion of carbon.

The project ECRA CCS ("ECRA CCS Project—Report on Phase III", European Cement Research Academy; Düsseldorf; March 2012) investigated the possibility of reducing $CO_2$ emissions by separation and storage of carbon dioxide. The combustion operation is to be switched to the oxyfuel process, and the offgases should be recirculated. This measure aims to stabilize the temperature and to increase the concentration of $CO_2$ in the offgas. The $CO_2$ concentration in the recirculated gas is 75 vol % to 82 vol %. The remaining constituents include inter alia carbon monoxide, water, oxygen, nitrogen, argon and chlorides and nitrogen oxides in very low concentrations. A portion of the recirculated offgas is separated, dedusted, desulfurized and purified of impurities such as nitrogen oxides, hydrogen chloride, hydrogen fluoride, mercury, other metals and other organic or inorganic substances, wherein the prior art CCS process would at this stage separate carbon monoxide without subjecting it to further treatment. After the water condensation, $CO_2$ is separated by cryogenic means. Carbon dioxide is subsequently compressed and transported to the underground storage site. The oxygen required for the oxyfuel process is obtained in an air separation plant.

When employing the process according to the invention, the described ECRA process is modified by compressing the $CO_2$-containing offgas to 0.8 MPa after dedusting, desulfurizing and removal of impurities. In contrast to the prior art process, freeing from CO and water is not necessary.

The compressed $CO_2$-containing gas is mixed with hydrogen to establish the stoichiometric ratio of 1:4 for carbon dioxide to hydrogen and of 1:3 for carbon monoxide to hydrogen.

The hydrogen is obtained on-site by high temperature steam electrolysis. The waste heat generated in the cement production is used to assist the electrolysis. The electricity required for the electrolysis may originate from renewable sources. The oxygen generated in the electrolysis is used for the oxyfuel process and an air separation plant is therefore not required in contrast to the prior art.

The gas mixture is supplied to a methanization reactor. The reaction is performed in the presence of nickel catalyst. An isothermic regime is preferred. The reaction heat is used in the cement production or for the electrolysis. After the separation of the methane where the methane is in particular separated from the water present in the gas mixture via a drying, and after being brought to quality specifications, the methane gas is fed into a municipal natural gas network.

The remaining residual gases such as nitrogen or argon and a very small amount of steam are discharged into the atmosphere.

At another location where hydrogen is for example required as a feedstock, methane (natural gas) is withdrawn from the natural gas network and subjected to pyrolysis. Methane is here cracked into carbon (carbon black) and hydrogen. A portion of the hydrogen is used as an energy source for the endothermic pyrolysis reaction. The other portion is used for example as a raw material for the chemical industry. The pyrolysis reaction may alternatively be operated with electricity.

Carbon is separated from gaseous hydrogen and collected. It is transported to the landfill site approved therefor and permanently and safely stored there.

Working Example 2: Treatment of Offgas From a Power Plant

The offgases from conventional power generation contain from 3 vol % to 15 vol % of carbon dioxide according to the coal type used for firing. Since firing is carried out with air, nitrogen and water form the remaining primary components of the offgases. The operating mode of the power plants is based on the optimal energetic utilization of the fuel. This has the result that the offgases contain 3% to 5 vol % of oxygen.

The fuels and consequently the offgases are contaminated with impurities such as sulfur compounds, nitrogen oxides, carbon monoxide and, not infrequently, with heavy metals.

In order to employ the process according to the invention for $CO_2$ separation, the offgas is cooled. This is followed in the next step by a dedusting and desulfurization and a selective, catalytic purification of impurities such as nitrogen oxides, hydrogen chloride, hydrogen fluoride, mercury, other metals and other organic or inorganic substances.

The purified offgas is mixed with hydrogen in order to establish the stoichiometric ratio between carbon dioxide and hydrogen of 1:4 that is necessary for the methanization. To this end the concentrations of carbon dioxide and hydrogen are subject to continuous online measurement. The consumption of $H_2$ is often higher than would be required for establishment of the stoichiometric ratio alone since hydrogen undergoes spontaneous reaction with oxygen in the offgas to afford water. It is therefore preferable when the proportion of oxygen present in the offgas is also determined.

The offgases of power plants are not typically pressurized and subsequent methanization therefore take place at atmospheric pressure. The reaction is carried out over a nickel catalyst at 300° C.-350° C. The offgases are subsequently cooled. Separation of methane is effected by means of an absorptive process. The oxygen present in the offgas is converted into water due to the addition of hydrogen. Storage of the methane may be effected by storage in a tank or by feeding into a municipal natural gas network.

The remaining residual gases such as nitrogen or argon and very small amounts of steam are discharged into the atmosphere.

At the location where hydrogen is for example required as a feedstock, methane (natural gas) is withdrawn from the natural gas network and subjected to pyrolysis. Methane is here cracked into carbon (carbon black) and hydrogen. A portion of the hydrogen is used as an energy source for the endothermic pyrolysis reaction. The other portion is used for example as a raw material for chemical production. The pyrolysis reaction may alternatively be operated with electricity. Carbon is separated from gaseous hydrogen and collected. It is transported to the landfill site approved therefor and permanently and safely stored there.

Working Example 3: Oxyfuel Combustion

Combustion both of fossil fuels and renewable fuels with air is prior art in combustion technology. In customary combustion operations, the offgases comprise 75 vol %-97 vol % of nitrogen after a steam condensation.

In the known oxyfuel process, combustion air is replaced by an oxygen-rich gas. In order to be able to control the combustion temperature of the offgases are recirculated. The addition of oxygen is 5 vol % to 20 vol % of the recirculated steam. The offgas, consisting of $CO_2$ and possibly steam but also of nitrogen, sulfur compounds and other impurities such as nitrogen oxides, hydrogen chloride, hydrogen fluoride, mercury, or other metals and other organic or inorganic substances, is discharged in the same order of magnitude. The steam is condensed out in a heat exchanger. After dedusting, desulfurization and purification of contaminants, $CO_2$-containing gas is available.

The oxygen required for the oxyfuel combustion is obtained in air separation plants. This makes the process energy intensive.

In the process according to the invention, the $CO_2$-containing offgas is dedusted, desulfurized and purified of impurities after cooling. The offgas is subsequently mixed with hydrogen so that the ratio of $CO_2$ to $H_2$ is 1:4. In the next step, the gas mixture is supplied to a reactor in which it is reacted over a nickel catalyst to afford methane gas. The reaction is carried out at a temperature of 300° C. to 350° C. and a pressure of 0.7 MPa to 0.8 MPa. The reaction is used for steam production. The water formed during the methanization is condensed out and the methane is separated from further components such as for example nitrogen and argon. After being brought to the appropriate quality specifications the natural gas is fed into the municipal natural gas network.

The remaining residual gases such as nitrogen or argon and very small amounts of steam are discharged into the atmosphere.

If the hydrogen required for the process is obtained in an electrolysis operation, the steam obtained in the methanization may be used as the starting material for the steam electrolysis. On account of its high temperature, the waste heat from the combustion operation is used for production of steam which is used in the steam electrolysis. The oxygen formed in the electrolysis in addition to $H_2$ may be used as an oxygen source for the oxyfuel process so that an air separation plant may be eschewed.

As shown in the preceding working examples, methane (natural gas) is withdrawn from the natural gas network at the location where hydrogen is required for example as a feedstock. The methane gas is cracked to afford hydrogen and carbon in a pyrolysis reaction. A portion of the hydrogen is used as an energy source for the endothermic pyrolysis reaction. The other portion is used for example as a raw material for chemical production. The pyrolysis reaction may alternatively be operated with electricity.

Carbon is separated from gaseous hydrogen and collected. It is transported to the landfill site approved therefor and permanently and safely stored there.

Working Example 4: Offgases From Crude Oil Refineries

The molar concentration of $H_2$ in offgases from crude oil refineries varies between 5 mol % and 90 mol %. The offgases further contain $CO_2$ (up to 8 mol %), small amounts of carbon monoxide CO (up to 2 mol %) and hydrocarbons, predominantly methane $CH_4$. This working example is exemplary for offgases where the proportion of the hydrogen present is dominant.

The offgas may consist of 60 vol % of $H_2$, 30 vol % of $CH_4$, 8 vol % of $CO_2$ and 2 vol % of CO for example. To establish the stoichiometric ratios $CO_2:H_2$ and $CO:H_2$, offgas from the steam generator of the oil refinery containing as substantial components for example 9 vol % of $CO_2$, 18 vol % of hydrogen and 73 vol % of nitrogen is used as additive gas.

After mixing of the two mass flows, the reactant mixture according to table 1 is thus introduced into the subsequent catalytic methanization.

TABLE 1

| | |
|---|---|
| $CH_4$ | 30 mol |
| $H_2$ | 60 mol |
| CO | 2 mol |
| $CO_2$ | 12.5 mol (8 mol from refinery offgas and 5.5 mol from steam generator offgas) |

TABLE 1-continued

| | |
|---|---|
| $N_2$ | 44 mol from steam generator offgas |
| $H_2O$ | 11 mol from steam generator offgas |

The offgas from the steam generator used as additive gas may also contain sulfur compounds and dust that are removed in the next process stage. The thus-treated $CO_2/H_2O/N_2$ mixture as additive gas is mixed with the hydrogen-containing refinery gas. The mass flows and concentrations in the resulting stream are continuously measured to establish a molar ratio between hydrogen and carbon dioxide of 4:1 and between hydrogen and carbon monoxide of 3:1. In the offgas of the example, 5.5 volume fractions of $CO_2$ are mixed with the additive gas.

The mixture is heated to a temperature of 300° C. which is advantageous for the methanization reaction. The methanization reaction may be performed at atmospheric pressure. At 80%, the reaction has a high selectivity. In order to increase the conversion efficiency it is advantageous to compress the reaction mixture to a pressure of 0.8 MPa.

The treated gas mixture is supplied to the methanization reactor. An upstream separation of the nitrogen is not required since the inert gas does not affect the selectivity and yield of the reaction. The reaction is performed in the presence of nickel catalyst. An isothermic regime is preferred. The reaction is used to produce steam.

After the reaction, the gas mixture contains 30 vol % of $H_2O$, 35 vol % of $CH_4$ and 35 vol % of $N_2$. The further workup comprises condensation of the reaction water and separation of nitrogen so that finally the remaining gas mixture consisting of methane and residual nitrogen attains the required quality and is introduced into the municipal gas network.

The remaining nitrogen and a very small amount of steam are discharged into the atmosphere.

At another location where hydrogen is for example required as a feedstock, methane (natural gas) is withdrawn from the natural gas network and subjected to pyrolysis. Methane is here cracked into carbon (carbon black) and hydrogen. A portion of the hydrogen is used as an energy source for the endothermic pyrolysis reaction. The other portion is used for example as a raw material for chemical production.

Carbon is separated from gaseous hydrogen and collected. It is transported to the landfill site approved therefor and permanently and safely stored there.

BRIEF DESCRIPTION OF THE FIGURES

Working examples of the invention are shown in the drawings and more particularly elucidated in the description which follows.

The following description of the working examples of the invention refers to identical or similar components and elements with identical reference numerals without repeated description of these components and elements in individual cases. The figures are a mere schematic representation of the subject matter of the invention.

Figure 1:
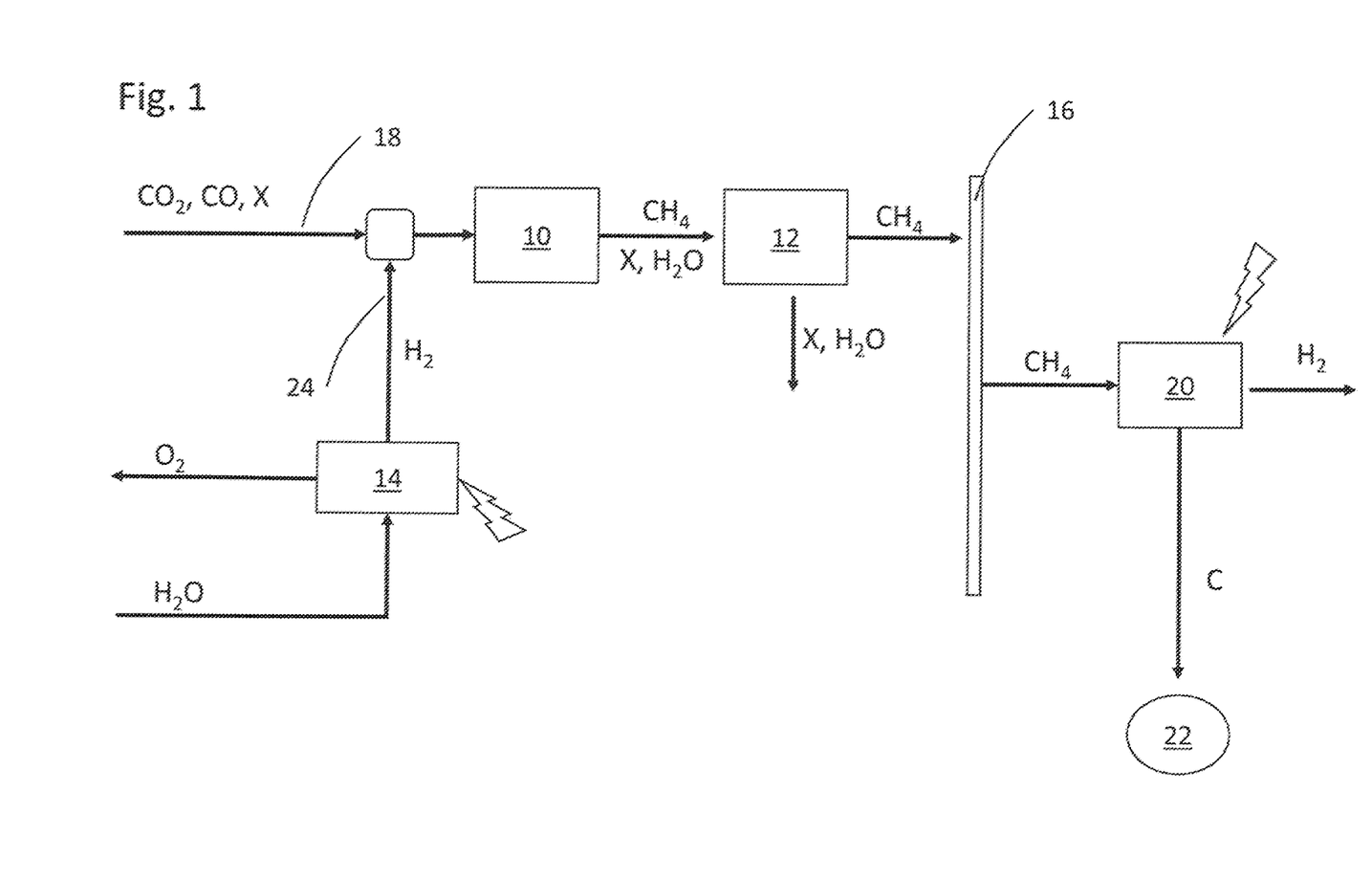
FIG. 1 shows a schematic representation of a first embodiment of the process where the offgas comprises an excess of carbon oxides and FIG. 2 shows a schematic representation of a second embodiment of the process where the offgas comprises an excess of hydrogen.

FIG. 1 shows a first embodiment of the process in which an offgas 18 rich in carbon oxides, which in the example shown contains $CO_2$, CO and further components represented by "X" such as nitrogen and argon, is mixed with $H_2$ as additive gas 24 to establish a stoichiometric ratio of $CO_2$ to $H_2$ and CO to $H_2$ which is optimal for a subsequent methanization reaction. The hydrogen $H_2$ is produced from water $H_2O$ using electrical energy via an electrolyzer 14. In the example shown, the oxygen $O_2$ likewise generated in the electrolysis is discharged into the atmosphere. Aternatively, the oxygen $O_2$ may also be supplied to a combustion operation to form the offgas 18.

The offgas 18 mixed with the hydrogen $H_2$ is supplied to a reactor 10 in which a catalytic methanization reaction is performed. Carbon dioxide $CO_2$ and hydrogen $H_2$ and also carbon monoxide CO and hydrogen $H_2$ react to afford a methane $CH_4$ and water $H_2O$. In a separation apparatus 12, the water $H_2O$ produced in the methanization and the further components X are separated from the methane $CH_4$. The methane $CH_4$ is subsequently fed into a natural gas network 16.

At the location where landfilling of carbon black C may be effected, the methane $CH_4$ is withdrawn from the natural gas network 16 and supplied to a methane cracker 20. In the methane cracker 20, the methane $CH_4$ is cracked into carbon black C and hydrogen $H_2$ by pyrolysis. The hydrogen $H_2$ is subsequently available for further utilization, for example as a starting material for the chemical industry or as an energy carrier.

The carbon generated in the form of carbon black C during the cracking of the methane $CH_4$ is stored in a carbon landfill 22 and thus permanently removed from the atmosphere.

Figure 2:
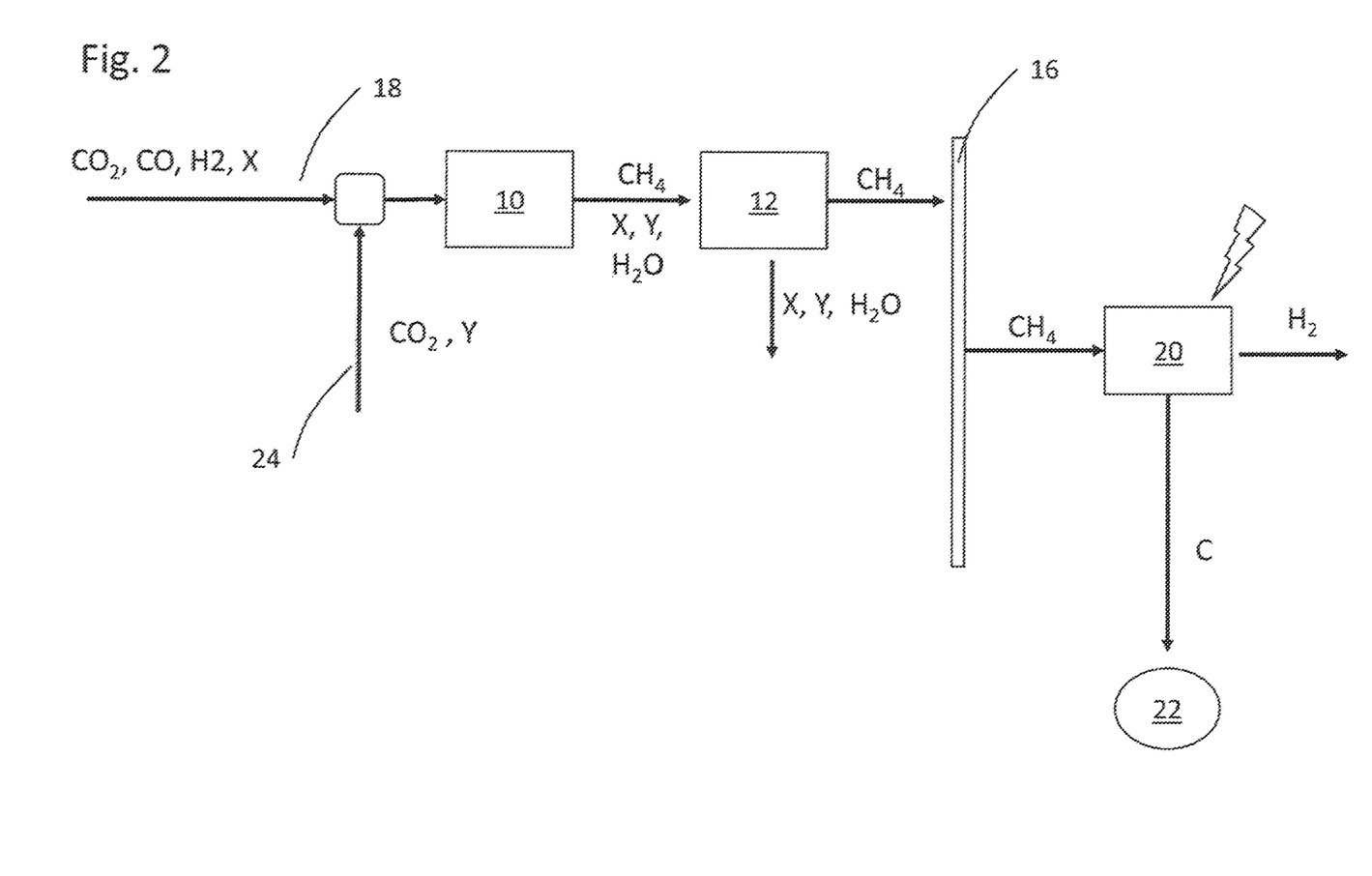

FIG. 2 shows a schematic representation of a second embodiment of the process. A hydrogen-rich offgas 18, which in the example shown contains $CO_2$, CO, $H_2$ and the further components represented by "X", is mixed with an additive gas 24 containing $CO_2$ to establish a stoichiometric ratio of $CO_2$ to $H_2$ and CO to $H_2$ which is optimal for a subsequent methanization reaction. The additive gas 24 may contain further components represented by "Y" such as for example $H_2O$ or $N_2$.

The resulting reaction mixture is supplied to a reactor 10 in which a catalytic methanization reaction is performed. Carbon dioxide $CO_2$ and hydrogen $H_2$ and also carbon monoxide CO and hydrogen $H_2$ react to afford a methane $CH_4$ and water $H_2O$. In a separation apparatus 12, the water $H_2O$ produced in the methanization and any further components "X" and "Y" present are separated from the methane $CH_4$. The methane $CH_4$ is subsequently fed into a natural gas network 16.

At the location where landfilling of carbon black C may be effected, the methane $CH_4$ is withdrawn from the natural gas network 16 and supplied to a methane cracker 20. In the methane cracker 20, the methane $CH_4$ is cracked into carbon black C and hydrogen $H_2$ by pyrolysis. The hydrogen $H_2$ is subsequently available for further utilization, for example as a starting material for the chemical industry or as an energy carrier.

The carbon generated in the form of carbon black C during the cracking of the methane $CH_4$ is stored in a carbon landfill 22 and thus permanently removed from the atmosphere.

The invention is not limited to the presently described embodiments and the aspects highlighted therein. On the contrary, a multiplicity of variations which are within the purview of those skilled in the art is possible within the scope specified by the claims.

LIST OF REFERENCE NUMERALS

10 Reactor
12 Separating means
14 Electrolyser
16 Natural gas network
18 Offgas
20 Methane cracker
22 Carbon landfill
24 Additive gas

The invention claimed is:

1. A process for separation and immobilization of carbon dioxide and/or carbon monoxide from an offgas, wherein the offgas is obtained by combustion of fossil fuels in a power plant, as a byproduct in an industrial process or as an extraction gas in the extraction of fossil fuels, comprising the steps of:
   a) establishing a stoichiometric ratio of carbon dioxide to hydrogen and/or of carbon monoxide and hydrogen which is suitable for a methanization reaction by supplying the offgas with a corresponding amount of hydrogen or alternatively carbon dioxide and/or carbon monoxide by an additive gas,
   b) performing a catalytic reaction in which the reactants carbon dioxide and/or carbon monoxide and also hydrogen are converted into methane and water,
   c) separating the methane from the product of the catalytic reaction, wherein remaining residual gases are discharged into the atmosphere,
   d) cracking the methane into carbon and hydrogen, wherein the carbon is generated as a solid,
   e) collecting the cracked carbon, and
   f) landfilling the collected carbon
   wherein the offgas is a mixture of at least two components, wherein the offgas comprises at least carbon dioxide or carbon monoxide as one component and the offgas comprises at least one inert gas as a further component which remains in the offgas after the separation according to step c),
   wherein to establish the stoichiometric ratio the proportions of carbon dioxide and/or of carbon monoxide present in the offgas are measured, wherein the proportion of hydrogen present in the offgas is optionally also measured.

2. The process of claim 1, wherein in step a) a stoichiometric ratio of 4 hydrogen molecules to 1 molecule of carbon dioxide and/or 3 hydrogen molecules to 1 molecule of carbon monoxide is established in the offgas, wherein in the case of an excess of hydrogen in the offgas an additive gas containing carbon dioxide and/or carbon monoxide is used and in the case of a deficit of hydrogen an additive gas containing hydrogen is used.

3. The process of claim 1, wherein the separation of the methane is effected by condensation, adsorption, or separation with membranes.

4. The process of claim 1, wherein the cracking of the methane is effected by a pyrolysis process.

5. The process of claim 1, wherein the cracking of the methane produces hydrogen and wherein the energy required for the cracking is provided by partial utilization of the hydrogen.

6. The process of claim 1, wherein the cracking of the methane produces hydrogen and wherein at least a portion of the hydrogen is used as a starting material in the chemical industry or as an energy carrier for the generation of electricity, heat, or as a fuel for vehicles.

7. The process of claim 1, wherein the methane separated in step c) is fed into a gas network and to perform step d) of the process methane is withdrawn from the gas network.

8. The process of claim 1, wherein the offgas is desulfurized, purified of other impurities, and/or dedusted in a pretreatment.

9. The process of claim 1, wherein the hydrogen supplied in step a) is produced by an electrolysis operation, wherein the oxygen likewise generated is supplied to a combustion operation in which the offgas treated with the process is formed.

10. The process of claim 1, wherein the carbon obtained as a solid is mixed with a carrier before the landfilling of step f), wherein the carrier is selected from loam, gravel, building rubble, slags, rocks, wastes, or a combination of two or more of these carrier materials.

* * * * *